US008817966B2

(12) United States Patent
Wrench

(10) Patent No.: US 8,817,966 B2
(45) Date of Patent: Aug. 26, 2014

(54) METHOD OF COLLECTING AND EMPLOYING INFORMATION ABOUT PARTIES TO A TELEVIDEO CONFERENCE

(76) Inventor: Lisa Marie Bennett Wrench, Fallbrook, CA (US)

(*) Notice: Subject to any disclaimer, the term of this patent is extended or adjusted under 35 U.S.C. 154(b) by 533 days.

(21) Appl. No.: 13/135,531

(22) Filed: Jul. 8, 2011

(65) Prior Publication Data

US 2012/0176466 A1 Jul. 12, 2012

Related U.S. Application Data

(60) Provisional application No. 61/399,281, filed on Jul. 8, 2010.

(51) Int. Cl.
| | |
|---|---|
| *H04M 3/42* | (2006.01) |
| *G06Q 10/10* | (2012.01) |
| *H04N 7/14* | (2006.01) |
| *G06Q 50/00* | (2012.01) |
| *H04N 7/15* | (2006.01) |
| *G06Q 50/22* | (2012.01) |

(52) U.S. Cl.
CPC ............ *H04N 7/147* (2013.01); *G06Q 10/103* (2013.01); *G06Q 50/01* (2013.01); *H04N 7/15* (2013.01); *G06Q 50/22* (2013.01); *G06Q 10/101* (2013.01)
USPC ................................. 379/202.01; 348/14.08

(58) Field of Classification Search
CPC ............ H04N 7/15; H04N 21/42201; H04N 21/4532; H04N 44/222; H04N 7/155; G06Q 10/1095; G06Q 10/1093; H04L 12/1818; H04L 12/1813; H04L 12/1822; H04L 12/1831; H04M 3/567; H04M 1/72569; H04M 3/42365; H04M 2203/5054; H04M 2203/5081
USPC ................... 348/E7.083–7.084, 14.08, 14.09; 379/202.01; 709/204; 705/7.19
See application file for complete search history.

(56) References Cited

U.S. PATENT DOCUMENTS

| | | | | |
|---|---|---|---|---|
| 8,131,800 | B2 * | 3/2012 | Bagley et al. ................. | 709/204 |
| 8,289,368 | B2 * | 10/2012 | Gopal et al. ................. | 348/14.09 |
| 2002/0122112 | A1 * | 9/2002 | Mallart et al. ............. | 348/14.08 |
| 2004/0161090 | A1 * | 8/2004 | Digate et al. ............. | 379/202.01 |
| 2008/0088698 | A1 * | 4/2008 | Patel et al. .................. | 348/14.09 |
| 2010/0149306 | A1 * | 6/2010 | Gopal et al. ................. | 348/14.09 |
| 2010/0251158 | A1 * | 9/2010 | Geppert et al. ................ | 715/771 |
| 2010/0315482 | A1 * | 12/2010 | Rosenfeld et al. .......... | 348/14.08 |
| 2011/0090301 | A1 * | 4/2011 | Aaron et al. .............. | 348/14.08 |
| 2011/0268418 | A1 * | 11/2011 | Jones et al. .................... | 386/200 |
| 2011/0307287 | A1 * | 12/2011 | Conley ......................... | 705/7.19 |

(Continued)

*Primary Examiner* — Mohammad Islam
(74) *Attorney, Agent, or Firm* — Kirk A. Buhler; Buhler & Associates

(57) ABSTRACT

A method for creating an intelligent routing and criteria-based matching system, so that people may be matched for conferencing to each other by pre-determined matching of their characteristics and their requirements. The invention makes it possible to connect individuals who may or may not have been known to each other previously, and who may be routed to each other based on being good fits to collaborate in the stated business or social setting or other reason for dealing with another person in a video conference meeting. The invention makes it possible for suppliers of services over the video conference medium to be connected to individuals who want these services. The system takes into account the business rules and preferences of all individuals involved, so that intelligent business service collaboration may take place between parties based on pre-set criteria.

31 Claims, 9 Drawing Sheets

TWO OR MORE INDIVIDUALS COMMUNICATING ON A VIDEO CONFERENCE

(56) References Cited

U.S. PATENT DOCUMENTS

| | | | |
|---|---|---|---|
| 2012/0069134 A1* | 3/2012 | Garcia et al. | 348/14.08 |
| 2012/0117153 A1* | 5/2012 | Gunasekar et al. | 709/204 |
| 2012/0150581 A1* | 6/2012 | McPhail | 705/7.19 |
| 2013/0145432 A1* | 6/2013 | Ristock et al. | 726/4 |
| 2013/0169742 A1* | 7/2013 | Wu et al. | 348/14.08 |
| 2013/0239025 A1* | 9/2013 | Aaron et al. | 715/756 |

* cited by examiner

METHOD OF COLLECTING AND EMPLOYING INFORMATION ABOUT PARTIES TO A TELEVIDEO CONFERENCE

CROSS-REFERENCE TO RELATED APPLICATIONS

This application takes priority from provisional patent application Ser. No. 61/399,281 filed on Jul. 8, 2010.

BACKGROUND OF THE INVENTION

Field of the Invention

The present invention relates generally to the field of video conferencing. The invention relates more specifically to the field of a software-based protocol for enhancing the effectiveness, efficiency and benefits of video conferencing communications.

With the proliferation of inexpensive Internet and wireless communication traffic, and advances in the ability to encode a signal for visual and audio for video traffic over these media, video conferencing is becoming an inexpensive solution for individuals to conduct meetings that would normally take place in a face-to-face or over-the-phone fashion.

Current state of the art in video conferencing, scheduling and invitation of parties to the call, rests upon the already existing familiarity of the parties of the call with each other, to one degree or another. For instance, a lawyer and his client may wish to conduct a video teleconference of their meeting. Or, a company may seek to have people on a video conference call together who do not actually know each other, but their names are known, or the departments in which they work, and the function that they will play in the meeting, are known in advance.

SUMMARY OF THE INVENTION

Software exists to allow an individual to turn a basic computer station, cell phones and other smart devices into video terminals, which can process video signals. This invention does not reside in the software controlling the signal or control of a device as an input point for video communication.

This invention is concerned with creating an intelligent routing and criteria-based matching system, so that people may be matched intelligently for conferencing to each other by pre-determined matching of their characteristics and their requirements. The invention makes it possible to connect individuals who may or may not have been known to each other previously, and who may be routed to each other based on being good fits to collaborate in the stated business or social setting or other reason for dealing with another person in a video conference meeting.

The invention makes it possible for suppliers of services over the video conference medium to be connected to individuals who want these services. The system takes into account the business rules and preferences of all individuals involved, so that business service collaboration may take place between parties based on pre-set criteria.

This invention incorporates a system, composed of user interfaces, templates for collecting data, and related databases, and other software, which is used to control the business workflow process and personalization of activities centered around video conferencing between multiple parties.

This system collects business logic, preferences, skills information and profile characteristics from the people who will be potentially matched for the video conference call. This innovative process allows individuals who may not know each other, but have demanded requests for services (such as consultation, advice, or needing a mediator or interpreter of a two-person interaction) or have requests based on wanting to communicate with someone who has similar likes and dislikes, or other profile characteristics, such as geographic, language, age, gender, education, professional experience, etc. to connect with each other via a video conference.

This disclosure also describes novel ways of collecting information and acting upon it, which results from feedback given to the video system by the participants of a video conference meeting. People participating in a call can give feedback about their satisfaction with both the content or services of the call, their ease of communication with the other parties, and their ability to collaborate well with the other parties involved in the call, as well as personally liking or disliking the person or way in which they provide services across the video medium.

This feedback can be used to create workflow processes for a Customer Relationship Manager, quality control, education of users of the system, and customized interventions or further collaborations between individuals both inside and outside of a video conference environment.

In the case of a video interpretation conference, a sign language interpreter will be present along with at least one deaf or hard of hearing individual (hereinafter "deaf") and one hearing individual. The sign language Interpreter participant facilitates the communication between the two parties, by using sign language (a visual language of movement of hands and gestures of face and body) and an oral language (i.e., English, hereinafter "English", although any spoken language would apply as well).

The current invention uses multiple collected identifying factors about the parties on the call (the deaf or hard of hearing person; the interpreter; and the oral language participant) and uses these identifying factors to assure that the correct parties are matched to each other.

The inventive method assumes that video conferencing involves at least two people, but can involve more than this number. It assumes that the electronic software utilized in making the video conference itself is generic and can be employed control decision-making about whom to connect to whom, and when, and how.

The inventive method enables individuals (or someone on their behalf) to place a user's unique characteristics into a user-account. The information can be collected by a third party on their behalf (such as by a hospital declaring that they have a patient/customer who has a particular need for interpretation in a particular language).

The present invention uses customizable business rule templates and personal profiling templates and content and feedback templates in combination to provide effective matching of people for collaboration and communication of a variety of types through the medium of video conferencing, and decision making prior to, during and after a video conference transaction.

BRIEF DESCRIPTION OF THE DRAWINGS

The various embodiments, features and advances of the present invention will be understood more completely hereinafter as a result of a detailed description thereof in which reference will be made to the following drawings.

BRIEF DESCRIPTION OF PREFERRED EMBODIMENTS

Figure 1:
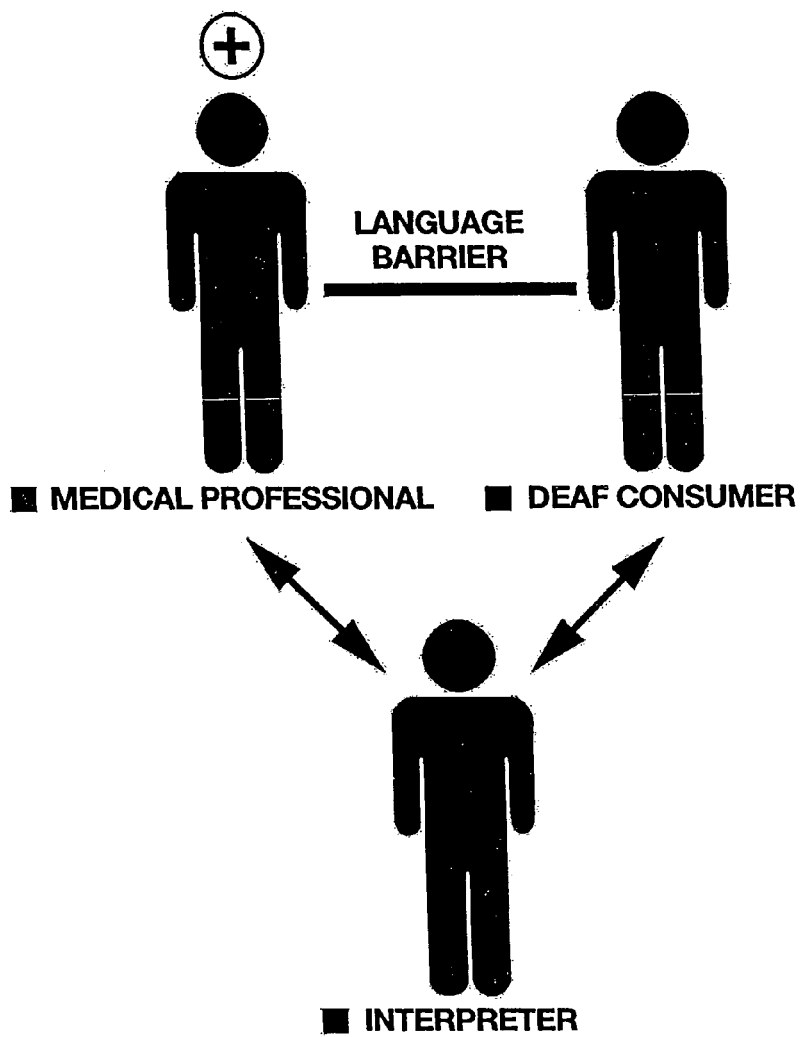
FIG. 1 is a schematic diagram showing the normal interaction between a medical professional and a deaf person and employing an interpreter.
Figure 2:
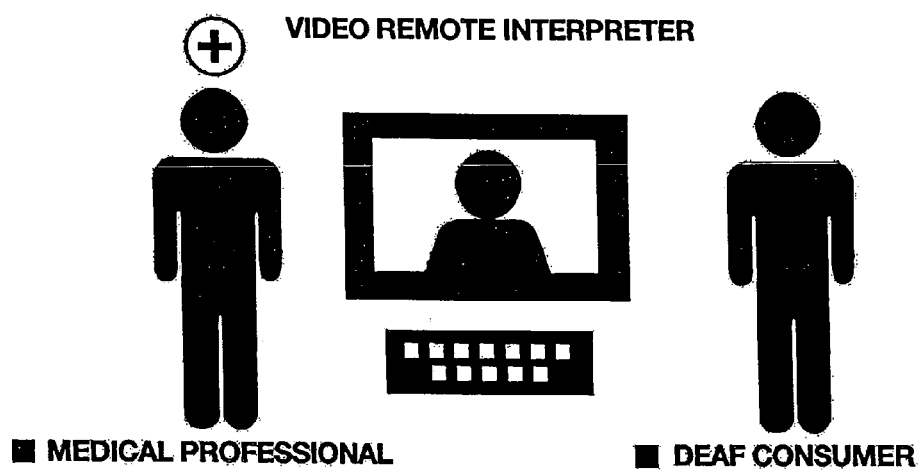
FIG. 2 is a schematic diagram showing the interaction of FIG. 1 wherein the interpreter is employed using a video remote system.
Figure 3:
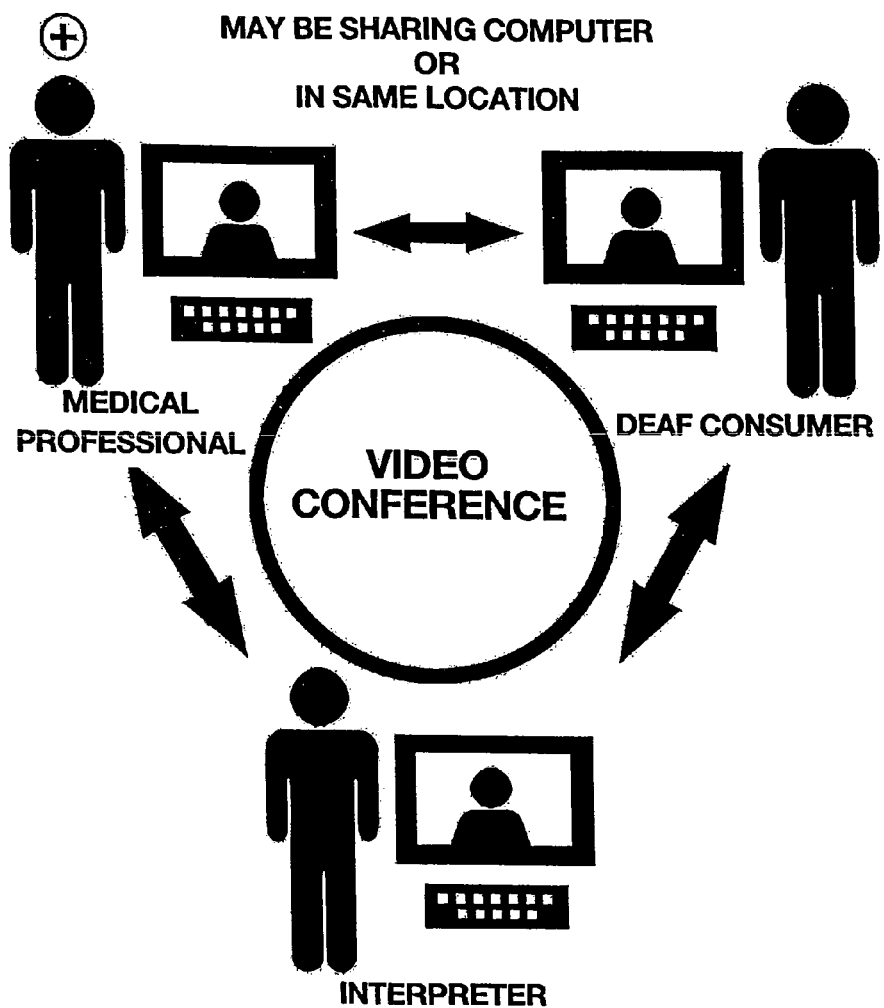
FIG. 3 is a schematic diagram showing the interaction of FIGS. 1 and 2 in which each participant utilizes a video communicating system.
Figure 4:
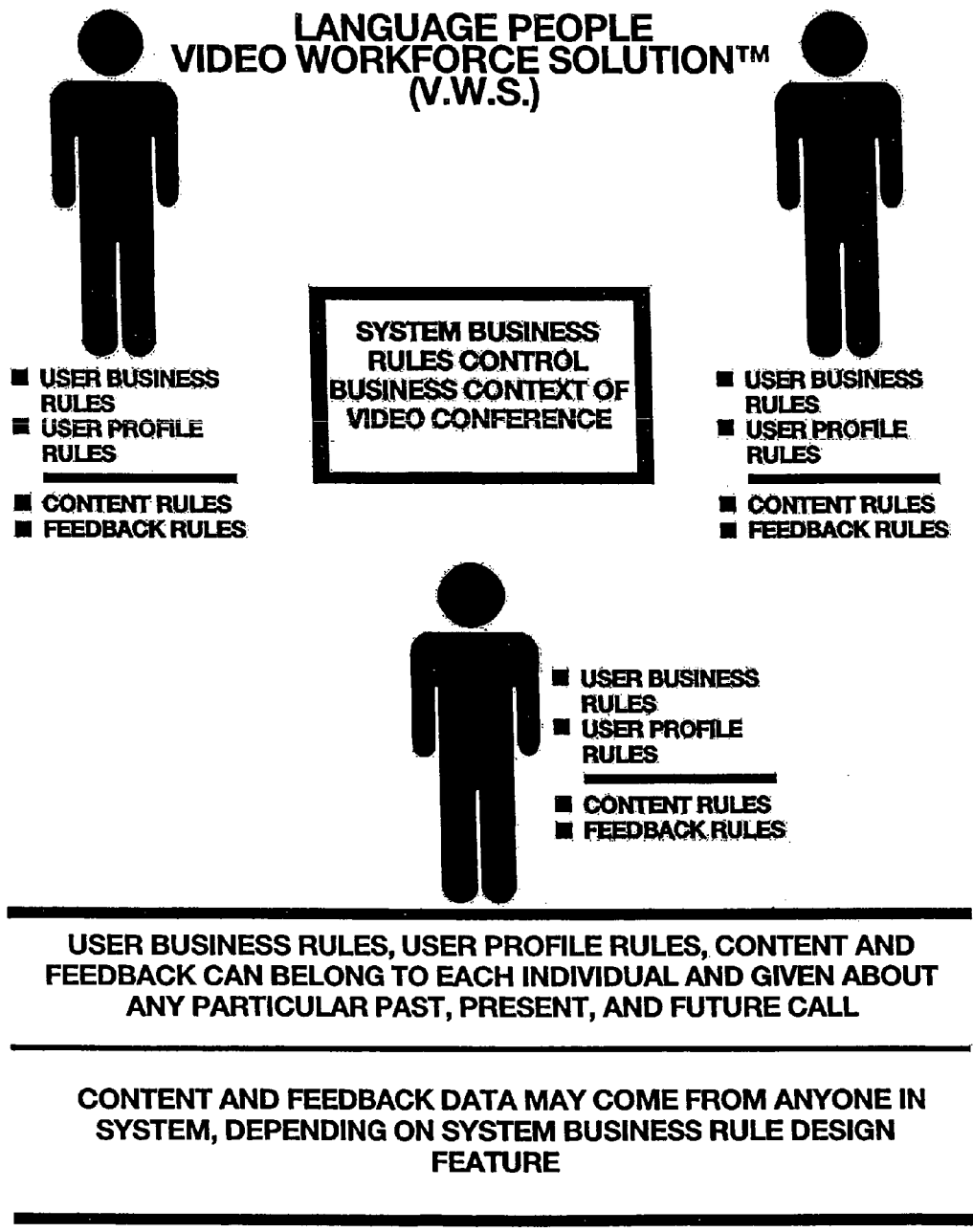
FIG. 4 is a schematic diagram indicating the various rules involved in the system of FIG. 3 that are provided in a preferred embodiment of the present invention.
Figure 5:
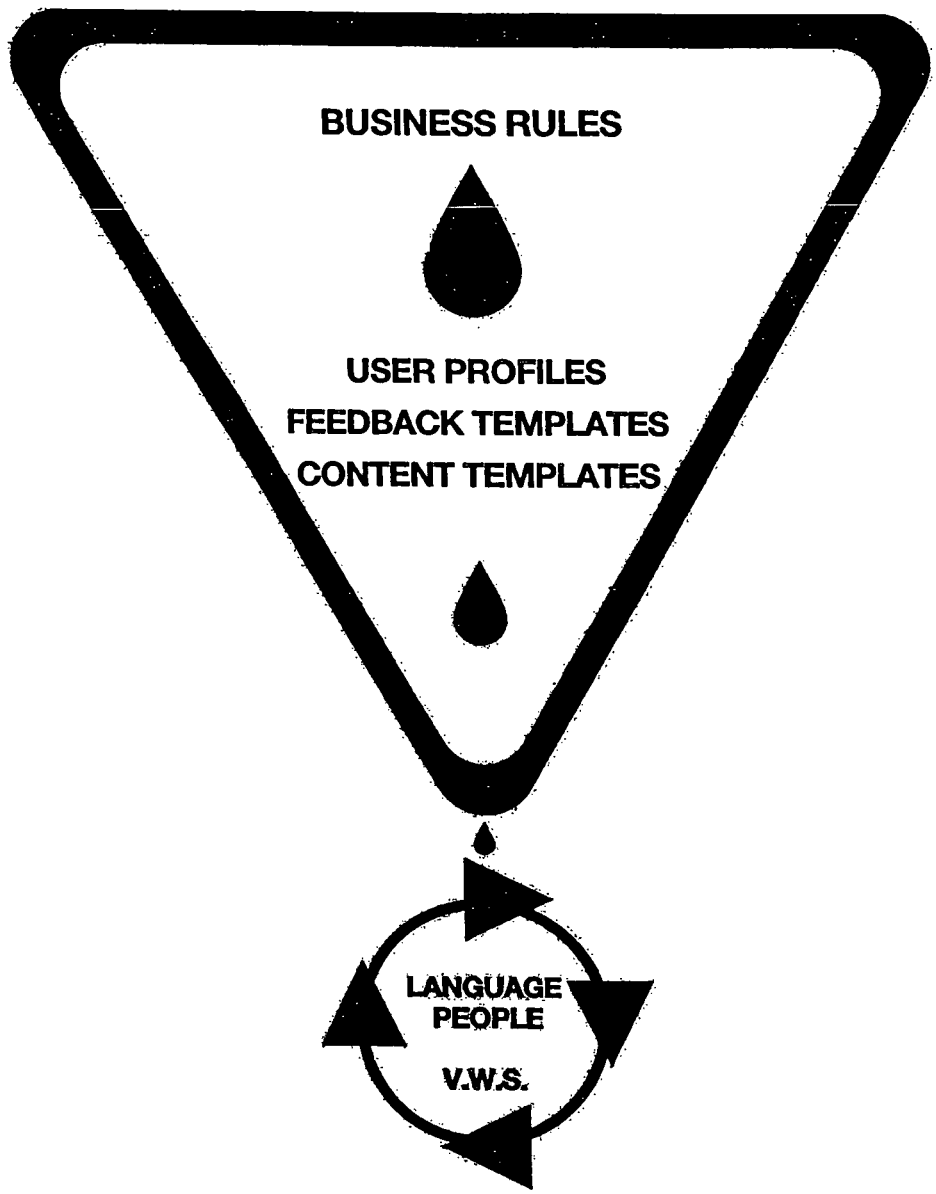
FIG. 5 is a schematic diagram illustrating stage 1 of the workflow of the present invention.
Figure 6:
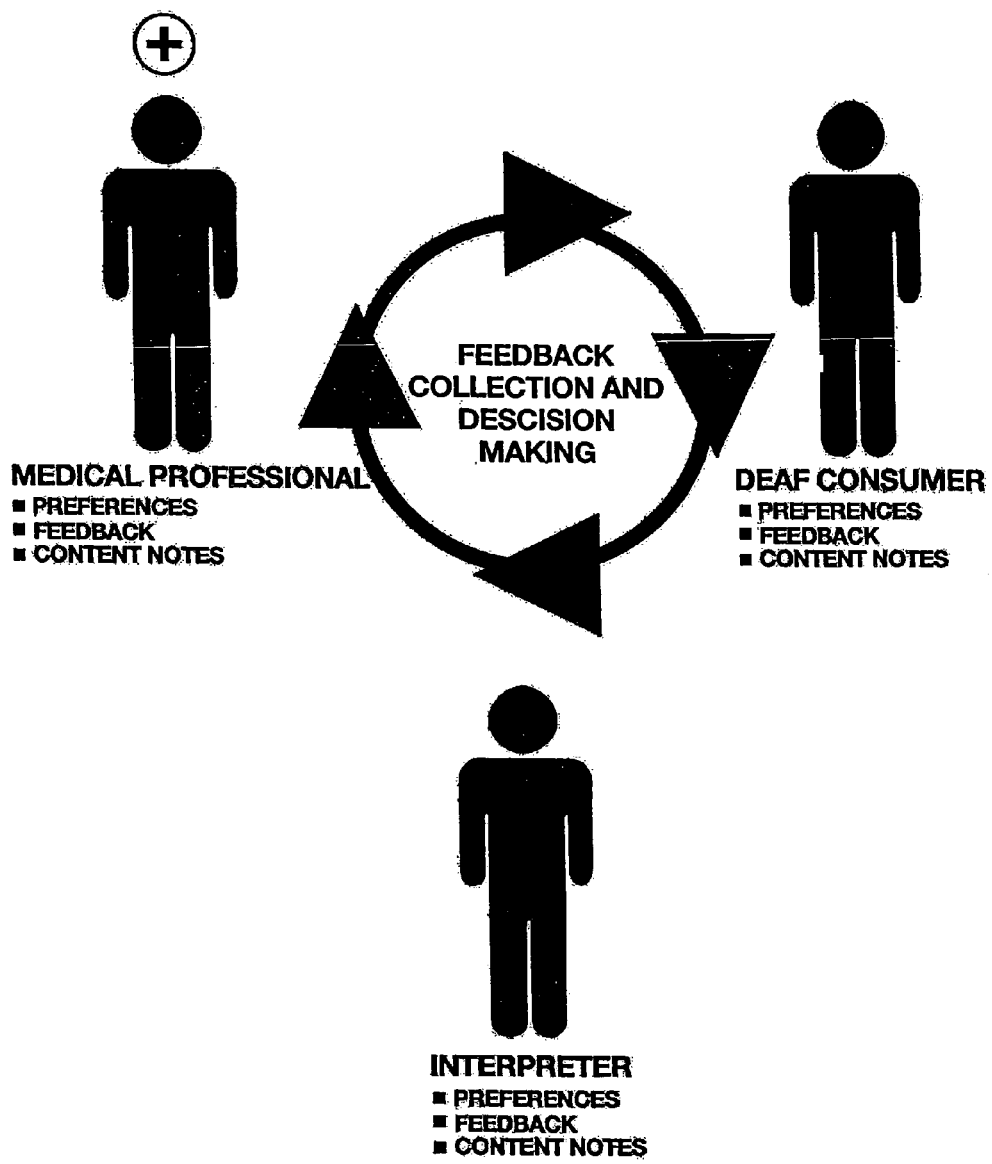
FIG. 6 is a schematic diagram illustrating user video workflow features of the preferred embodiment of the present invention.
Figure 7:
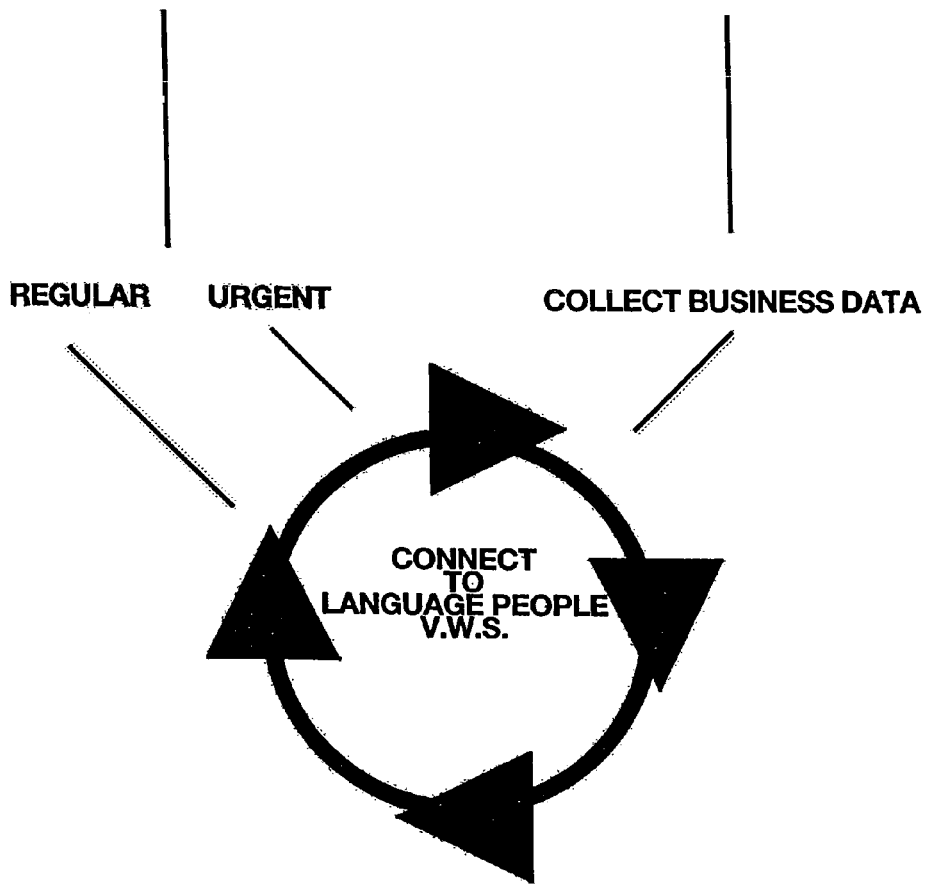
FIG. 7 is a schematic diagram illustrating video workflow in a more generalized embodiment of the present invention.
Figure 8:
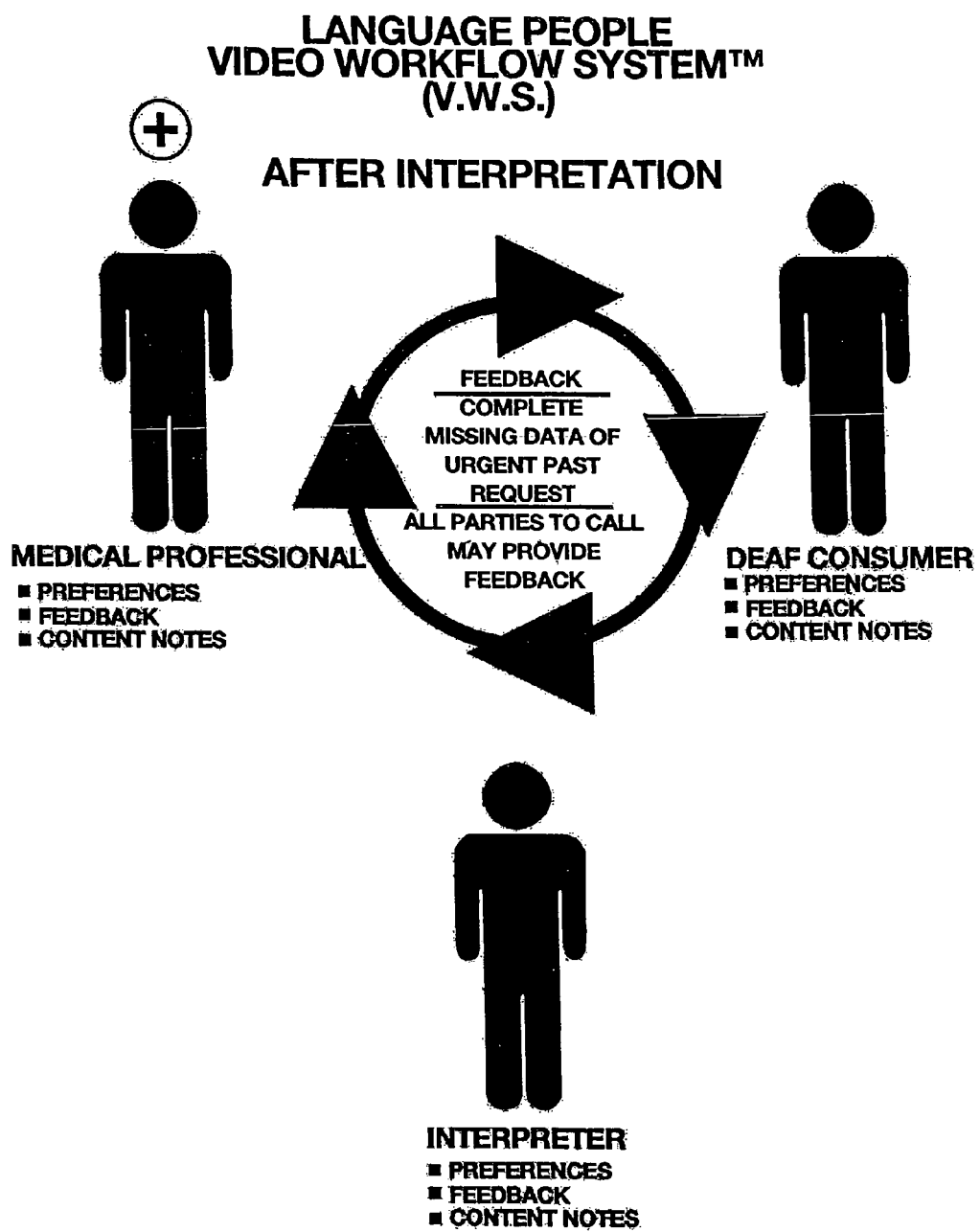
FIG. 8 is a schematic diagram illustrating the various characteristics of the present invention which may be utilized after an interpretation has been completed.
Figure 9:
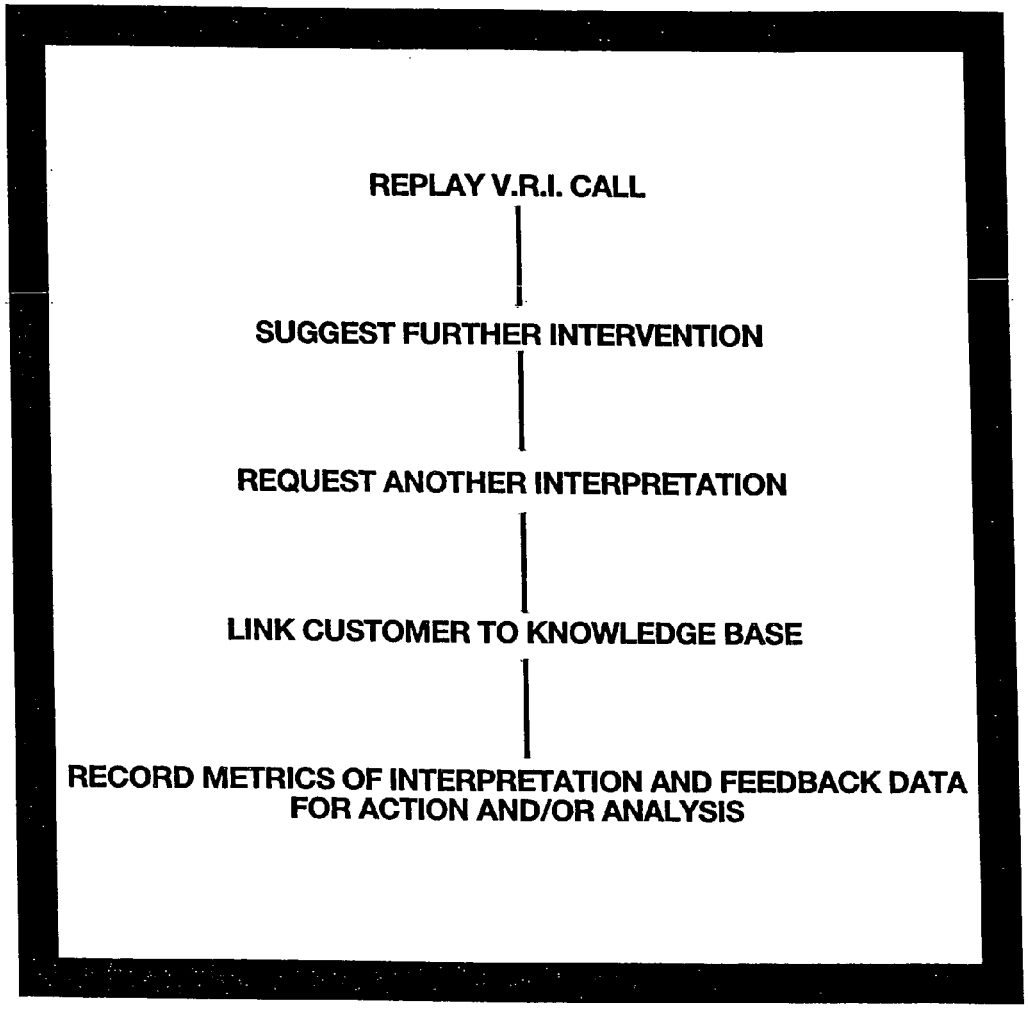
FIG. 9 is a schematic diagram illustrating various "next actions" which may be utilized as features of a preferred embodiment of the present invention.

The present invention comprises a method for promoting more effective communication and collaboration between people by correctly matching them as compatible within a video conferencing environment.

An important factor in whether individuals will communicate effectively is whether they understand each other's language. This system takes into account variables related to language as part of the filtering process of who to connect to whom in a video conference transaction.

There are various factors that control whether individuals can communicate with each other. These include accent, dialect, regional word vocabularies, etc. There can be wide variations which can affect communication issues. Some of the issues the present invention solves involve such language issues and the ability to profile people so that optimal communication is achieved.

Additionally, people's ability to work together or understand or be satisfied with an interaction can be based on personal preferences of many kinds.

Model of a Video Conference Transaction

In any video transaction, there are two or more aspects of the transaction that are occurring:

1) The individuals involved are attempting to do something together. This "something" can range from meeting each other for social reasons to conducting a business activity with each other.

2) People are requesting to be connected to each other based on preferences which they feel are important in order to be able to communicate or collaborate.

The present invention involves the use of Customizable System Business Rule templates which control the business logic at a system level of what will happen before, during and after the video conference. System Business Rules (SBR's) are based on mirroring process-steps which would need to take place between the parties relative to the activity that they are engaging in at the "doing something" together level, whether this activity would be taking place in a face to face meeting, over a phone, or over a video conference call. The System Business Rules Templates control the "who-what-why-and-when" relative to connecting people to each other within the video conferencing system. The business rules also control the variables which deal with the real-time logistics of connecting people on a video call (examples could include but not be limited to: How long can the call be? Who is available to be connected? How long should the system wait for an available person to connect before moving onto offering the connection to another individual?, etc.).

The invention uses User definable Business-Rule Templates (UBR's) which allow users of the system to define under what conditions they agree to participate in a video conference. Their choices of conditions flow out of the parameters of the system business rules as stated above.

An example of system and User Business Rules would be that a video conferencing system could be used so that a law firm's lawyers could consult with their clients over video conference. The business rules which pertain to legal activities of lawyers would be included in the video system's business rules (SBR's). A particular lawyer might only want to consult with clients who would pay them over $100 per hour, or between the hours of 8 AM and 5 PM in their time zone. These would be User-defined business rules.

The present invention also makes use of Profile Rules Templates, (PR's) which are templates which mirror the characteristics relative to the person in the video conference transaction (Item 2 above). These customizable templates determine what information should be collected relative to the personal characteristics of the users of a system, based on the business rules inherent in the overall video conference system. Using the legal consulting example above, a Profile Template would customize the system so that information about an attorney's credentials and areas of specialization would be collected by the system as personal characteristics.

The overall business case upon which the video conference is being conducted, will determine the contents of the Business Rules Template within any specific video conferencing system as described herein. The profile characteristics of the users within the system flow out of the Business Rules Template and business case for which the system is designed.

Business Rules and Profile Templates are used to collect, store and act upon data which users or their agents enter on their behalf for purposes of making relevant matches of individuals to conduct video conferences using the present invention, and drive workflow processes.

Additionally, in any video conference, the subject matter of the activity, as well as the participant's qualitative assessment about what the conversation will be, or was about, are important variables in an effective transaction. Thus, the present invention makes use of Content Templates, and Feedback Templates. Content Templates are customizable and are defined by the same individuals who are in charge of the Business Rules Templates. An example of Content Tables would be the ability of a lawyer to store information that described that the meeting was an initial client meeting or a pre-trial client meeting. Or, using the same Content Tables, a lawyer could also store notes about what took place in the meeting. Such notes about a meeting can be collected and stored in a history fashion. Permissions for who can see what histories (i.e., an attorney can see all histories of all clients, or only their own clients) are collected and controlled.

Another example of the use of a Content Table to collect situational variables would be that an attorney could view that a client was requesting counsel, and the subject of the conversation would be representation on a murder charge. Notes could say that the charges include alleged murder of a child. An attorney could select not to participate in that video consultation based on that information about a situational variable in a Content Table. Another example of a Content variable would be that a lawyer could decline participation based on a conflict of interest, as a Content variable in a legal video conferencing application would be who the intended other party in any lawsuit might be.

Feedback Templates are customizable and control what information is obtained by the users of the video system after a video session. This may be ratings about how the participants felt the video conference did or did not meet their needs, or in the case of a lawyer above, answers to feedback questions could trigger further steps in a workflow process. An example would be that a lawyer could say that he felt that his client adequately understood the counsel that he gave (or not) and depending on this answer, the client could be scheduled for another interview, or sent information about the area of law involved, or directed to a knowledge base about this area of law.

This invention incorporates a system, composed of user interfaces, templates for collecting data, and related databases, and other software, which is used to control the business workflow process and personalization of activities centered around video conferencing between multiple parties.

The present invention uses customizable business rule templates and personal profiling templates and content and feedback templates in combination to provide effective matching of people for collaboration and communication of a variety of types through the medium of video conferencing, and decision making prior to, during and after a video conference transaction.

Dynamic "Queue" Populations Based on Template Variables and Real-time Variables.

The placing of individuals into groups of queues for a video or telephone call is present technology. Logging whether someone is available or not available is part of existing business practices.

However, using the invention's Templates to determine who could be placed into a "queue" (group of people) as a potential match for a particular video call, is a novel feature. In the case of this invention, all of the variations in business rules and preferences (as well as feedback and content) which can be called into play based on any one unique situation, create, in effect, a novel and dynamic "Queue System" wherein individuals can be selected as 1) matching and 2) 'opting-in' to be on a call, and from this potential group of people, participants on the video call may be connected to a particular call. Real world variables such as availability to be on a call at a particular time can also be considered to queue, and schedule video conferences that meet the "business" requirements and preferences of the parties who may be joining a video conference call, and could be customized based on the System Business Rules in place.

Collection of Time Based and Other Information about the Video Call

The present system includes features which will record such objective information as who was connected as a party to a video call, how long the call lasted, on what day and time the call took place, and other variables about the routing history and connection of the call (did the call go to various departments, and not get answered and then route finally to another person or Queue, when and how did parties enter and exit the video conference?).

Video Conferencing for Interpreting—Example of a Preferred Method of the Invention This example of a preferred method of the invention relates to the use of this invention to connect people in a video conference for the purpose of providing interpreting services. An interpretation generally has two or more people in the transaction who use different languages, and an interpreter, who is a bilingual (or multilingual) individual who facilitates communication between the two or more people who have different languages.

Video interpreting is very effective for individuals who are deaf or hard of hearing and use a sign language for communication. This example of a preferred method of the invention uses the example of a Video Interpreting Matching System for connecting deaf individuals whose language is American Sign Language (ASL) with an American-English hearing person through an interpreter who is fluent in both ASL and spoken English.

Sign language is a visual language which involves hand gestures, body language, and facial expressions to convey words and grammar. It does not use sound for meaning as do spoken languages.

There are multiple sign languages, just as there are multiple spoken languages. A few examples of such languages are American Sign Language, Australian Sign Language, and Spanish Sign Language. The gestures involved in each of these can be different to represent the same "word meaning", just as words are different for a concept in different spoken languages.

Additionally, sign language is a body-oriented language, and every person's body gestures are different as they make the movements that comprise a "word meaning" in sign language. An analogy would be that different people can be following an exercise instructor in a class in time to music, and each person will perform the movements similarly but with a different variation or style, and rhythm.

Additionally, sign language has a grammar, various types of "style" and "regional dialect" between people who use the same language. Using American Sign Language, (ASL) as an example, various "style" differences of grammar include Signed Exact English, Pigeon Signed English, etc. Some individuals use ASL signs, but in an English-word order because they learned ASL after learning English, and so their grammar is more "English" than pure ASL.

There are regional differences in American Sign Language because the language has evolved regionally. These variations of language can be significant, and are similar to variations of dialect within spoken languages. A hand-gesture in ASL for "strawberry" may be entirely different in Seattle, Wash. than it is in Washington, D.C. These communication differences can impede understanding between individuals who have the same American Sign Language background as a whole, but who learned ASL in different regions of the country, or now live in different regions.

All of the above mentioned factors can affect whether two individuals can communicate effectively, even though they may share the same language of ASL.

Thus, in the present invention, the method allows for collection of profile characteristics about users of the language—their gestural style, their dialect or regional characteristics, their grammatical style, etc. This allows more effective matching of people to be able to communicate effectively and understand each other throughout a conversation.

Additionally, in the case of Interpreting as a profession, there are various laws and regulations that control the profession of interpreting. Along with National Certification in America by RID (Registry of Interpreters for the Deaf) there exist non-uniform state laws and other policies which control how and when someone is qualified to interpret for a deaf individual. Worldwide, certification or professional licensure requirements vary widely.

Because a video conference can connect people from various different geographical areas on a call, various legal requirements could come into play if a deaf person was in one location and the interpreter in another, (for instance, deaf person in Texas, with hearing person in California, interpreter in Colorado). In this example, effective matching of individuals based on legal or other regulatory issues may also come into play based on the region where each member of the call is physically present.

The subject of the meeting or situational variables (i.e., a school setting, legal meeting, medical appointment) may also affect the requirements of who can legally interpret in that type of situation. Thus, various certifications or licenses held by the interpreter are only applicable to certain types of situations in which they are qualified to interpret.

Additionally, various vocabularies exist within professional areas. An interpreter must have familiarity with the vocabulary of a particular subject matter in which they are working—for instance, medical, legal, scientific, or other specialized vocabulary familiarity. If the subject matter of a video conversation is going to involve medical terminology, an interpreter must have this vocabulary in order to effectively facilitate communication.

To sum up, language variables, geography, skills, credentials, legal requirements and vocabulary can all directly impact interpretation services.

Additionally, human variables exist which affect how well people work together. The present invention allows for the ability to personalize the matching of people based on these characteristics.

Because of the variations of language, within the greater language of American Sign Language, for example, combined with the variations person-to-person of how they make these body gestures (recall the example of the Exercise Class above) various deaf individuals will communicate better with certain individuals and not with others, in terms of ease of communication and understanding each other.

This preference is significant to the communication ease between individuals, and applies not only between two deaf individuals communicating, but as importantly, between a deaf person and the individual who is interpreting for them. Because of these individual variations, deaf individuals may have preferred and non-preferred individuals in regards to interpreters. Interpreters will also have individuals for whom they do (or do not) believe they would be a good communication facilitator. This preference is very important to facilitate communication optimally between the deaf individual and a hearing person.

The present invention takes these variations in language, dialect, sign style, vocabularies and skill sets, professional qualifications and preferences (can work with, do not wish to work with) into account as profile characteristics. Individuals can be profiled or can self-report these characteristics or be verified for them. In this way, an interpreter can be matched to a deaf individual who would communicate well with them.

As is apparent from the above discussion, a combination of variables about people and their characteristics (language, skills, likes, dislikes) as well as variables about the situation inherent in the reason for a video conference meeting, (i.e., an interpretation of a medical appointment) are both necessary to accurately match and control workflow processes before and after a video conference.

These personal preferences can be collected by individuals prior to a video call to help facilitate communication matching by using the User Profile templates and Content Templates. The feedback portion of the invention using Feedback Templates and Content Templates also makes it possible to store information about a video interaction that has already occurred, and whether or not it was a good match, and whether the participants feel that they would work well together again, or do not wish to be connected together again. This is discussed more fully below.

In summary, the present invention collects a wide variety of personal profile characteristics from the various parties who have access to the televideo conferencing system, via self-report, testing, or validation of skills, credentials, etc., and places this information into data bases which are structured according to a customized template design based on the business rules of providing interpretation in a medical care situation. The invention uses this information in order to match on these characteristics, as discussed above.

Creation and Collection of Business Rules and Context and Contextual Information Using the example of interpretation, where a video call involves the activity of a person interpreting between two or individuals of different language, there are two distinct activities taking place:

1) there is a provision of interpreting services by an interpreter, between a deaf and a hearing person(s)
2) there is a conversation or service which is being provided which is the primary function of the interaction between the hearing person and the deaf person. This could be a business (medical consultation) or a non-business event (social interaction).

In both of the above cases, there are business rules and workflow processes involved in the provision of goods and services, or involved in the interaction. This conversation may be taking place in a hospital setting, a doctors office, a legal meeting, or some other venue. Relative to activity 1 above, there is often a compensation paid to the interpreter for their services in this transaction. In the case of activity 2 above, based on the reason for the meeting, if this is a service meeting, whoever is providing services to the other party (in this example a hospital to a deaf consumer) the provider of services has their own business rules which control the activity. This video conference transaction may be part of a larger workflow process of interaction with the other party. (as an example, a hospital may conduct a patient examination using an interpreter, and based on information from the meeting, schedule more tests, referrals, prescribe medication or examinations with other specialists). If the meeting is a business-oriented meeting, whoever is providing goods or services will wish to store and collect information which will help them customize the workflow and CRM and information gathering process pertaining to the provision of this service. This information becomes part of the business rules associated with the transaction.

In this application of the invention, creation of the Business Rules Templates involves business rules for both activities 1) and 2) above. As discussed previously, these business rules operate at a high-level to control the business rules of the system itself. Secondary Business Rule Templates (User Business Rule templates) can be created which define the business rules relative to the individual participants in the video conference.

In the present example, there will be two business services conducted. One is the provision of medical services. The other is the provision of interpreting services by one party in the system to another. The activity of providing medical care is the primary activity relative to the video conference. Therefore, the primary Business Rule Templates will control variables relative to the provision of medical services via the video conference. The secondary Business Rule Templates determine what requirements must be met on the part of each individual party in order for them to be connected on a video call for interpretation. An example of a secondary business rule would be that a system could be designed such that after selecting who would be a potential match (members of a queue for this call) the party to satisfy all criteria who answered first would be selected. Another criteria could be that if an exact match was not available to get onto a video call within 30 seconds of a request (i.e., request for an interpreter matching the criteria for the interpretation), that a "good enough" match of people would be made, and a person from that queue of available interpreters would be selected.

Additionally, the User Business Rules would be customized to the current application of the invention, so that the user or someone on their behalf, may enter the criteria and conditions under which they are willing to be involved in a particular video conference.

Each party to a video conference can create business rules which describe the conditions under which they are willing to participate in the video call.

At the system business rule level, a hospital could control when and how a video interpreting request is made of the system. Additionally, a hospital or service agency could provide business rules which control how they compensate or quality-control, or otherwise monitor participation of doctor, nurse or other staff participating on the video call. For example, an outside consultant to the hospital could be paid based for performing a consultation to the patient (for which an interpretation was being conducted). These billing rules would be part of the system business rules.

Generally, the party defining the system business rules may be considered the Initiating party (for this example, the hospital providing services is requesting interpreting services on behalf of a deaf patient and thus would be the initiating party). The hospital's business rules and logic would control various non-personal aspects of the workflow of the video call and how the actual recording of the call or the data collected within it, or afterwards, would be processed and controlled.

Another example would be a deaf individual who sells insurance, and who wishes to hire an interpreter to conduct a business meeting with a hearing insurance prospect. In this case, the deaf individual would be able to state the business rules under which they would initiate a request for a video interpretation through the video conferencing system.

It is important to note that every party to a video transaction (or who has access to the system) may pre-profile themselves, their User Business Rules, and their User Profile Rules. Together these control their characteristics and preferences, and with whom they do business, so that these variables are available for matching even before a video call has taken place. An example of this would be that a deaf consumer could register their user profile preferences into the video system, and give unique identifying information, and also state that they use a particular hospital for medical services. A hospital might have patient information about that individual in their own system. The present invention would be able to do a suggested match of preferred interpreter without violating patient confidentiality.

Collection of Content, Situational and Contextual Variables of the Video Conference In a video interpreting situation, as in other applications of the present invention, individuals who are going to be interacting for the first time may be connected to each other. In the case of interpretation, the content of the meeting, subject matter, and contextual variables and relevant past history previous to this conversation are all important information to help familiarize the interpreter with what should happen during the current interpretation event. Additionally, in the case of a medical interaction, the provider of services also wants to have information about the situational variables under which they are seeing this patient.

The present invention allows for the collection of relevant information and statistics regarding the transaction, which can be collected through the Content and Feedback Templates discussed above. These templates can provide each party with information about the subject matter of the meeting; about what is expected to happen during the meeting, and about what happened during the video conference, and what should happen next, if anything. Having the ability to to know ahead of time the context for an interpretation, as in the present example, is very important, as it helps to rapidly orient the interpreter as to the situation with which they will be dealing. Taking the example of a hospital seeking an interpretation for their medical consultation with a deaf consumer, we have the following:

1) hospital or service agency—data the system may collect could include (but not be limited to) consumer ID (i.e., deaf patient), their "phone number or IP address), what billing account this will be charged to within their system (generally necessary if they are paying for the transaction); who amongst their staff were on the call; how long the duration of the call was, and what department or service area of their enterprise was involved in this call.
2) The situational context of the video conference—i.e., a physical, or a surgery, or a discussion of test results regarding a biopsy could be communicated prior to even connecting the call. Based on this information, an interpreter would know the context of the call, and could "opt out" of providing interpreting for that session if they felt that they were not the right person to facilitate content of that subject matter (perhaps they had a relative recently die of cancer and did not feel they would be able to be a neutral communication facilitator on that particular day). Or the interpreter might feel that they did not have the background to work in that aspect of medical interpreting.
3) The content variables could help the interpreter to understand very quickly what would be the context of the video interpreting conference in which they would be participating.
4) Deaf individual—information collected may be their "phone number, IP address of their Internet computer", their sign style, region, dialect of language, who they prefer or do not prefer as their interpreters (this is from their profile) length of the call, who the service provider (#1 above) was.
5) Interpreter—length of call, who the #1 individual was above, #2 individual above, and information about how and if they will be paid for their services in this regard.

In the above example of three parties, the business application area of the present invention collects valuable information based on each party's characteristics and the information that they believe is necessary to be collected in order for them to effectively participate in the transaction.

The hospital may decide that they have various pieces of information that they feel are necessary for them to collect from the transaction, and to input into the system during or prior to commencing the video transaction, in order to be able to account for this transaction inside their own business. In this regard, the present invention allows each customer (i.e., the hospital above) to decide what information they wish to collect on their video calls in the system. For example, a hospital might decide that Patient Record #, Dr. ID, Department of their hospital and Accounting Budget # are all important information to collect when making a video call. The present invention allows them to have a User Profile which they can customize to collect this information.

Requirements Matching

The present invention allows the above customer (i.e., a hospital) to create a template which creates User-defined Custom Fields for Data Collection which is part of the Business Rules Template. It also allows each user or group user to set their own defined requirements into the model for matching through the User Business Rules Template process.

For instance, a hospital may decide that only interpreters who have 5 years or more of medical interpreting experience are qualified to interpret video calls for their patients. Or, that interpreters with a particular certification or degree or tested knowledge of medical terminology are qualified to interpret for their patients.

Another instance of such requirements matching, is that deaf consumers may state that they only want to have interpreters who are certified by RID to interpret for them. This information would be collectable and actionable based on the User Business Rules which depend on the System Business Rules available. A deaf person may prefer a person of a particular gender or other known preference, such as someone that they have worked well with before, or someone who matches them in terms of understanding sign gestures/style. These are User Profile characteristics.

Another instance of this requirement is that interpreters may profile themselves to say that they are only willing to take calls during a particular time frame, or for a particular compensation amount, or that match their sign language style, certification or vocabulary experience, or other stated preference. Such other stated preferences could be situational—i.e., they are only willing to interpret for mental health appointments, or legal appointments, and not for prison incarceration appointments. These would be User Business Rules. The interpreter can also set preferences about whom they wish to interpret for—both on the customer (hospital) side and on the individual (deaf person, for example) side These would be stored as User Profile Characteristics.

Various laws regarding criteria for whether someone is qualified to interpret professionally, can also be pre-determined and entered into the system requirements variables, and used to effect who provides interpreting for a particular call outside of these User-Defined Requirements matching via System Business Rules for interpreting for sign language in the locality (i.e., United States) where the Video Interpreting System is in operation.

Business Workflow Matching

Not all televideo interpreting requests occur on-demand. Instead, various future meetings between the deaf individual and the English speaker will be conducted. In this case, the present invention allows the future scheduling of requests for interpretation by the system. This forward-looking aspect of the present invention can be used in the following ways:

1) Each individual in the system can have a calendar of their past, present and future transactions in calendar or statistical format.
2) A scheduling system can be used to store, remind and "start-up" the video interpreting session.
3) A scheduling system can be used to alert an individual that there is no interpreter available at that time to meet their requests (over-demand status for individuals matching their needs).
4) System can suggest a time that such an appointment for interpretation could be conducted based on an absolute match between the preferences of all parties (based on requirements matching above) or a "good enough" match (user could de-select desired requirements of the proposed match to allow for a less refined match).
5) Individuals who would be parties to the video conference/interpretation can access information about proposed meetings, and view committed meetings, and adjust their schedules to accommodate a suggested meeting time.
6) Each party can have a calendar showing their committed meetings and related data.
7) Messaging to text devices, pagers, or cell phones to announce that a meeting is about to take place so that all parties are ready for the meeting.

Feedback about the Meeting

The present invention enables each party to the video conference to express feedback as to how they felt the interpretation/meeting went. For instance, after the video conference event, the system can automatically ask each participant to give feedback about the meeting through a survey on their video conferencing station. This information is collected and acted upon via the Feedback Templates in the system.

Recall that there are two activities going on simultaneously in the video interpretation/conference. Questions regarding the effectiveness of the interpretation services can be presented, as well as questions regarding the effectiveness of the underlying subject of the video conference (in this example, a hospital appointment). A pre-selected list of questions can be provided to each participant (about whether or not they felt that they achieved their objectives during the meeting, and whether the quality of the services provided by the interpreter met their needs, or did not, and whether they wish further actions to be flagged for review—another interpretation, or notification of the service provider, etc.

In this way, for instance, a hospital can collect relevant statistics about whether a deaf person felt:

1) the service by their doctor was good, excellent or less than adequate;
2) that they felt their questions had been answered adequately;
3) that they felt that the interpreter had provided them with adequate or excellent services;
4) that they would prefer or not prefer to work with this interpreter again;
5) other variables that would indicate their feeling of satisfaction with the transaction could be included which would be available for survey through the customer (hospital's) template provided to the system in advance.

In the same way, a doctor could give feedback:

1) they felt that the interpreter met their needs or not;
2) they felt that the deaf patient understood them well;
3) they felt that they would work again with that interpreter or not;
4) they could recommend that the deaf person avail themselves of other services to further enhance their understanding of the situation regarding their care (i.e., the next area of this discussion, collection of subject matter relevance and replay of video conference).
5) they could ask that this interpreter not be connected in an interpreting transaction with them again for whatever reason, or that they would like to have this interpreter work with them again in the future.

Additionally, the interpreter in this situation would have the ability to provide feedback as well:

1) they felt that they were able to understand and communicate well with the deaf individual;
2) they felt that the deaf patient was able to understand the content of the discussion adequately;

3) they felt that they would work well again with this deaf individual, or this doctor (or not);
4) they could flag this interaction as being in their opinion not completely satisfactory—in their professional opinion, all questions were not answered, or they felt that the deaf consumer was not completely grasping the content or the interaction, or they felt that something else had "gone wrong" with the interaction and that follow-up should occur between the parties;
5) they could give feedback requesting not to be connected in an interpreting transaction to this deaf individual again for whatever reason, or that they would like to work with this deaf individual again.
6) they could state a preference to not interpret for the hearing individual again, or that they would prefer to interpret for this hearing individual again.

Collection of Subject Matter Relevance and Replay of Video Conference

Through a combination of subject matter relevance in the Content Templates and feedback statistics from the Feedback Templates available to the users as discussed above, workflow routing can be done for the participants.

As an example by collecting either before hand and/or afterwards information from the participants about the subject matter of the video conference, (Content Templates) participants can be directed to a knowledge base that will provide more information regarding the content of the interpreted meeting. For instance, in the case of a medical appointment at a hospital being interpreted to a deaf patient at the hospital, the hospital in their customizing of their Business Rules Templates may elect to store what type of illness or treatment or body area this interpretation was related to. In that case, they may use this information stored in the system to direct their patient to videos, written materials, or other help regarding this general subject matter.

Another example would be that if an interpreter was rated as "not preferred" by a doctor or deaf person, quality control, or additional training could be a workflow routing based on feedback criteria from one or another of the other participants about the interpreter.

A hospital staff member who was rated as less than satisfactory on communication skills (by either an interpreter or the deaf person) could be routed to cultural or sensitivity training, or some other QA monitoring.

Recording of Conversations and Business Rules concerning Access to Playback and Content History The Business Rules logic and Content Template logic can provide automated permissions and workflow logic relative to when, who and how information can be viewed which is stored in the video conferencing data archives. Recall that this Invention matches people to each other for video calls, but it also collects information in data archives which provides meaning about the video call itself.

In this example of the invention, conversation may be recorded, and played back by the participants so that they can recall what was discussed and review them at a future time. Such a recording can also be used for other purposes, such as quality control or training. This information can be stored by data servers connected in the video conferencing system, and accessed by individuals who (since their information was collected at the time of the conference) were involved in the transaction. Access to this information can also be part of the business rules at the Business Rules level as well. This information would be available in a data storage archive that indexes each video call as being related to a particular data set of information about it. Additionally, at the Customer Business Rules Level, permissions may be set which allow others to view this data, or not based on the Customer Business Rules variables set up in the system.

In the present example of the invention, the ability to profile the parties to a 3-way service call involving interpreting for the deaf has been discussed. The additional business service of a hospital providing medical treatment to a deaf individual is the business-case reason for the video conference. Various aspects of information that is necessary in order to facilitate intelligent routing of that call, based on skills, language, dialect, region, and other factors have been discussed.

The present invention takes the current state of the industry of interpreting, which is primarily to match people based solely on language, and provides other criteria which can be collected from all three parties, and then called into play to meet legal requirements, vocabulary requirements, preferences, and other issues for a more effective communication match.

The example above discusses three individuals interacting together. It should be noted that there could be more than three people involved in a transaction, and it could be only two in terms of the more general application of the invention, matching only two people based on selected preferences.

A significant feature of the present invention is that all 3 parties can profile themselves and create their own business rules and User Profiles for participating in the interaction, and that each of the parties can be given access to the Content and Feedback areas, so that all of the parties interacting on a video call may contribute valuable information, or make decisions about whether to participate on a particular call, or with particular individuals, and under which circumstances, in future video meetings.

Yet another feature of scheduling an interpreting session in the present invention is the ability to send all parties in a video conference which is scheduled in advance, a text message or a reminder over the phone, or an email, that they are going to be in a meeting at a particular time, or emailing them to give feedback or put contents into the system.

In addition to providing a video interpreting solution for deaf individuals, the present invention can also solve the problem that exists that a deaf patient in a hospital who pushes a "Call" button through an intercom to a nurse's station or other location asking for help cannot use this verbally-based system to get help.

In addition to providing interpretation, the present Invention can create an intercom connection and alerting message to the computer at the nurse's station, to alert them that a deaf patient in a particular room or bed in the hospital needs help.

The deaf patient or the nurse could then initiate a video event with interpreting, or could use menu items to tell the nurse what they needed. These items would be contained in the definition of User Business Rules of the system, as defined in the System Business Rules general custom features.

This "alert" from a deaf person would be available to alert police, fire, or other individuals monitoring the needs or safety of a deaf individual in other applications of the present invention. One example would be the "call attendant" feature of an airplane. A deaf person with a computer or thin client device could communicate on a plane with the attendants that they needed help. Additionally, they could watch public-safety announcements or safety guidelines for flying on the same device.

Other Applications of the Invention

The invention more generally is a method for intelligently connecting individuals who want to reach others for communication or collaboration, or to conduct business, based on matching preferences, skills and other criteria, within the context of a video conference medium of communication exchange. By collecting preferences and profile information, and conditional business rules, one can intelligently connect individuals to each other on service requests and for collaboration or who just simply desire to interact together socially or meet new people who have similar likes and dislikes.

Another application of the invention would be in the area of legal consultation via video conference. Individuals needing legal help could be routed to attorneys who have matching professional expertise and other characteristics. These criteria could include but not be limited to the following:

1) Professional experience in a particular specialty or type of law;
2) Regional certification or other professional qualifications;
3) Gender;
4) Willing to work for a particular fee amount;
5) Do not already have conflicts in representing other customers.

In this application, an individual could profile themselves as a consumer needing legal help. They would disclose who could potentially be the other side of a lawsuit and what type of matter the subject was, and what they were willing to pay per hour/event to obtain consultation.

Legal Consultation Example

Attorneys or firms could match themselves and their legal staff and what they were willing to work for (profile and business rules). They could provide their client list into the system as part of their business rules, to enable them to instantly know whether they had a legal conflict before giving advice to the individual requesting services, and take or not take a video conference call based on those criteria.

Further, because the system records the time, duration of the call, and who was on the call, service industries such as law firms can do billing for their legal time through the call statistics. They can collect statistics as to which department, what aspect of law, etc.

Additionally, because they can store the type of subject matter of the video call within the system, they can direct their client to their knowledge base of subject-relevant information. Further, they may record the call and make that information accessible to the consultee or themselves for further uses, and in their business rules control access to the information of the call as regards attorney/client confidentiality.

This application of the invention can include using preferences regarding to whom they would like to be connected and who they would prefer NOT to be connected to—for instance attorneys will have conflicts of interest. Potential clients may know that a particular attorney is not to their liking, and they can list that individuals' identity as someone that they prefer not to be connected to in the system. Preference data collected during feedback as described above in the Interpreting example could also be used for rating services of a provider, QA control of one's staff of service providers, etc.

Dating, Consulting and Social Collaboration System Example

The present invention can be used to provide a matching dating system, or where people would like to discuss or collaborate on projects based on profile characteristics.

In the present example, individuals who are profiled in terms of personality and preferences can be matched to each other to communicate for social interaction, dating, collaborating on projects, etc. User Profile Templates can be used to match people who would likely wish to meet. Content Templates would help people understand what would be taking place in that meeting. An example of a dating site would be that content or situational variables could be things such as "prayer meeting" "bible study" "coffee" or "discuss Tom Sawyer" and individuals could choose to connect or not based on the content of the meeting.

Feedback templates for a dating site could be used to give feedback about both whether the meeting itself was enjoyable, and via Preferences Templates whether that person would like to video conference again with the other individual(s) on the video call.

If on-going meetings were to be continuing between parties, content and notes could give new participants important information about past video calls related to a current one so that they could be up to speed on the current discussion.

In a social or business conferencing system, Business Rule Templates and User Business Rules could determine how video conferences and the underlying transactions of what the activity of the meeting is should be handled. Individuals may be "service givers" or equals in a community in this example. For instance, perhaps someone is a therapist, or a giver of advice, or a life coach. This individual can be matched as a service provider with individuals who want this service over televideo conference.

Since statistics such as region, subject matter, gender, or other profiling characteristics are flexible to the users of the system, matching across video conferencing can be accomplished using user profiles. If there is a fee-for service model for use of the video service, then individuals may select as User Business Rules whether or not they are to be billed for their time as part of the business rules of their participation in the system (i.e., an advice giver) and whether they are willing to pay for the other party's time (i.e., a consumer of advice services). Connection to various electronic charging systems (Pay Pal, credit card, etc.) can be connected to the billing statistics of the system.

Again, in this kind of example, the ability to utilize feedback about the interaction, (satisfaction survey, etc.) and the ability to connect to knowledge bases on similar subject matter, can be facilitated by the collection of information about the subject matter of the video conference, as well as the re-viewing of the conference itself.

With respect to a social or collaborative agenda for a video conference meeting, a perception of whether or not the social context of the conversation was achieved, was or was not potentially enjoyable, would also be a factor that could be available for feedback and collection, and well as rating of helpfulness of the service provider. These statistics could be used to provide new service consumers with an indication of the service rating of an individual service provider based on the ratings of others who have used the services. This could be displayed to a potential consumer prior to their making the call (this would be the case with any service industry—law, therapy, astrology, dating, etc.).

In regard to a dating site using the video system, obviously data about the characteristics, personality and physical appearance of an individual would also be available as profile information. An astrology or club video conferencing site would also be storing information in their customizable user-profile template relative to the subject matter of their group.

Inmate Monitoring, Home Health, Education at a Distance, and Other Non-Face to Face Interaction Uses By providing an individual with an access point to the video system, such as a computer, video camera and software to effect the conference call, individuals who would normally be monitored or communicated with by a phone call or physical visit could be communicated with and/or monitored via video for safety, compliance, or health or other reasons where they do not wish to engage the person in person, but where they would like to physically see the person as well as hear their voice as they would if they were on a phone call.

Additionally, it is possible to control on what type of device the video client software is available, and in this way, one can verify that an individual with whom they are communicating is physically in the location they expect them to be. This would be helpful to know in cases of monitoring physical presence.

Elder Home Care

One application area would be monitoring the elderly at home, and using a video conference to ensure that they are safe, healthy, happy and remembering their medications, eating well, feeling well, or other such concerns. The feedback area of the system could be used to give information back to the monitoring or healthcare provider or that further intervention might be necessary.

Video Medical Care

Another application would be video-remote healthcare, wherein someone might have a communicable disease, or be released to home after surgery. In this application, a doctor or nurse would check in with the individual at home. For example, a doctor can have a patient demonstrate that they have use of a limb upon which a surgery was performed and that the tissue of that limb looks healthy. It would also be possible to use the feedback aspect of the system to collect pertinent data regarding patient compliance and wellbeing. Such feedback data could be used to trigger more intervention, encouraging the individual to use the knowledge base, or other uses. Recording of the video conversation would allow the individual at home to replay the advice or instructions given, or to access the knowledge base regarding their condition and how to improve their care outcome or what dangerous signs or symptoms to watch for regarding their condition, or how to take prescribed medications.

Law Enforcement

Another application area would be the ability of Law Enforcement or probation officials to put people on "home arrest" and interview them via video camera instead of by phone for compliance with the requirements of their legal situation. Again, the feedback loop and recording features of the present invention could be useful to provide evidence of compliance, non-compliance, or other information important to the agency involved.

Communication and Education for the Incarcerated

Another application would be providing access to education for individuals who are incarcerated, or family and friends communication. The video system would allow for the appropriate control of who when, how and under what conditions individuals were connected to people outside the prison for video communication, and the recording of the statistics of who used the system (incarcerated individual) would allow the prison system to verify that they were providing appropriate access to educational opportunities or communication access to family members, etc. through the video system. Regarding deaf incarcerated persons, such video communication would be an equal access right of the deaf, since hearing prisoners are allowed phone calls under controlled circumstances.

Another application would at "at-home schooling" where teachers could help at home students who needed help in various subjects. Attendance of group classes and duration of time spent on the call would be collected, as well as video "face to face" interview by the teacher and multi-student collaboration projects. Students and teachers could be matched based on their profile characteristics, and rate their interactions with each other through the feedback aspect of the invention for a variety of uses. As with other applications of the invention, connection to knowledge bases, and control of workflow processes can be achieved based on the results of the assessments of the teacher and student during the feedback portion of the video system.

In all of these instances the aspect of someone in the interaction perhaps being a "service provider" of a business service on which charges could apply could be created through the customization of the business rules controlling the video conference between the parties. For instance, the doctor or nurse making a call to a patient at home, the officer or probation official making the call, or the teacher helping a student—could all be paid or have their employment managed through the business rules attached to the video system. This would include the billing aspects of the system, as well as service providers being rated for their effectiveness in providing the services through the system.

Connection or Comparison to Other Demographic Statistics

Feedback loops that exist within the present invention may also be tied to online knowledge bases, CRM systems and other data systems, which could measure other customer behavior outside of the interaction on the televideo conference. Data collected on who the caller was, and their profile statistics, could be compared to other behaviors or interaction they may have with the provider of the video conferencing service.

An example of this would be the ability to compare data collected from web purchases by an individual and their ratings of satisfaction with a customer service agent via a video conference call. These types of comparisons of individuals and aggregate data could be especially meaningful to a provider of goods or services in understanding relationships between customer service and ultimate purchases.

As another example, a prison could measure rehabilitation outcomes of incarcerated inmates or compliance with rules, compared to access to video conferencing visitation with family or others outside the prison.

As another example, a hospital could collect statistics of what diagnoses, or treatments their video medical service customers had been involved in, and compare this with treatment outcomes, and perception of doctor/nurse-patient relationship as compared to those who did not have services via video conference.

Multiple Roles in the Use of the Video Conferencing System

In the present invention, it is assumed that individuals may participate in a number of video conference communities or service areas. In one instance, they may be a lawyer providing legal advice to consumers through a video conferencing system provided by their law firm. In another instance, they may be the receiver of services of medical consultation across video.

The present invention could be used where a person and their preferences could be stored in a large multi-function communication video conferencing population, or where their profile would be dependent upon the business rules and situation-based variables controlling the actual underlying activity for which the video conference was conducted.

An example of the differences would be that a person could be both a service provider registered in a community system (as in the case of being on a consulting attorney website) and a patient within a particular hospital's database. Their preferences in each situational role would be different. Both databases would not necessarily be congruent, as patient information is confidential. Alternatively, as has been discussed in the E-clarity, Inc. U.S. Pat. No. 7,478,035, large anonymous profiling of users for transaction matching could be performed using the present invention to connect individuals to each other for a video conference.

Thus it will be seen that the present invention comprises a method for interconnecting participants to a video conference in an intelligent manner based on prepared rules, profiles, preferences and needs. The invention has been disclosed herein using various examples and illustrations of embodiments to explain the nature of features thereof. However, the scope of the protection is defined by the appended claims.

I claim:

1. A computer-based method for matching prospective participants of a televideo conference; the method comprising the steps of:
   establishing conference rules based upon the business criteria to which the purpose of the televideo conference is related prior to initiating said televideo conference;
   wherein said conference rules include determining a service required by a first participant;
   providing at least one template having fields to be completed with data based upon said service required by said first participant to establish at least one parameter to connect said first participant with at least a second participant wherein said first participant requires skills, professional background or needs from said second participant;
   using a feedback database from said connection thereby;
   forming a rule database of prospective participants based upon the conference rules and data in the fields of said template;
   selecting participants of said televideo conference from said feedback database and said rule database, and recording said televideo conference as a workflow.

2. The method recited in claim 1 further comprising the steps of conducting said televideo conference and having said first participant and said at least a second participant generate an evaluation of the quality of the interaction, the people, the information shared, or variable associated to the video conference transaction and adding said evaluation to said feedback database.

3. The method recited in claim 2 further comprising the steps of: storing information collected by at least one participant in a database related to said televideo conference;
   employing said stored information to determine what beneficial product or service should be delivered to said first participant.

4. The method recited in claim 1 further comprising the steps of conducting said televideo conference and offering all participant of said conference to generate feedback concerning the remaining participants and adding said feedback to said feedback database.

5. The method recited in claim 1 wherein at least one of said participants of said conference includes at least one of a group comprising of is an attorney a healthcare provider, a specialist, a doctor, a health care worker, a provider of goods, an insurance provider, a social interaction person, a provider of services and a translator.

6. The method recited in claim 1 wherein using said recorded workflow as an agreement to perform medical or legal services for said first participant.

7. The method recited in claim 1 wherein at least one of said participants of said conference is an interpreter and at least two other of said participants utilize different languages both of which are understood by said interpreter using said preference database to optimize participant satisfaction.

8. The method recited in claim 1 wherein at least one of said participants of said conference does sign language, video captioned English or other form of interpreting and wherein at least one other of said participants is deaf or hard of hearing using said rule database to ensure preferences legal and regulatory compliance.

9. A computer-based method for selecting participants of a video conference; the method comprising the steps of:
   establishing conference rules based upon the purpose of the conference to create an agreement for future services;
   providing at least one template having at least one field to be completed with data being related to at least one parameter regarding a participant's skills, preferences, licensing, personality, gender, geography, personal data or needs;
   forming a database of prospective needs participants and providers participants based upon the conference rules and data in the at least one field of said at least one template;
   and selecting needs participants and providers participants of said video conference from said database to ensure legal and regulatory compliance.

10. The method recited in claim 9 further comprising the steps of conducting said video conference and having said first participant and said at least a second participant generate an evaluation of at least one aspect of the conference and adding said evaluation to said database.

11. The method recited in claim 9 further comprising the steps of conducting said video conference and offering each selected participant of said conference an opportunity to generate feedback concerning the remaining participants and adding said evaluation to said database.

12. The method recited in claim 9 wherein at least one of said participants of said conference includes at least one of a group comprising of an attorney a healthcare provider, a specialist, a doctor, a health care worker, an insurance provider, a provider of goods, a social interaction person, a provider of services and a translator.

13. The method recited in claim 1 wherein using said recorded workflow as an agreement to perform medical, or goods, or services, or legal services for said first participant.

14. The method recited in claim 9 wherein at least one of said participants of said conference is an interpreter and at least two other of said participants communicate in different languages both of which are understood by said interpreter using said database to optimize participant satisfaction.

15. The method recited in claim 9 wherein at least one of said participants of said conference does sign language and wherein at least one other of said participants is deaf or hard of hearing or uses captioned language assistance using said database to ensure preferences legal and regulatory compliance.

16. The method recited in claim 9 wherein the video conference subject relates to monitoring the present and past health, safety or location of at least one of the participants.

17. The method recited in claim 10 wherein at least one of the participants is an expert in a selected field and wherein the expert participant interviews one other participant in the selected field during said conference and stores data relating to said interview.

18. The method recited in claim 10 wherein at least one participant of said conference is a known source of certain information discussed during said conference and at least one other participant wishes to learn said certain information from said source during said conference.

19. The method recited in claim 9 wherein at least one of said participants relies on preferences of other of said participants to decide whether to take part in said conference and adds additional feedback to said database expressly or by association.

20. The method recited in claim 9 wherein at least one of said participants relies on preferences of other of said participants to permit or block participation by said other participants and using said permit or block participation to add to said database.

21. A method for matching participants to a video conference based upon selected criteria including professional skills, nature of services and purpose of the conference; the method comprising the steps of:
   a) establishing a set of business rules relating to conferences wherein said business rules comprise regulatory, geographic, licensing or legal business rules;
   b) establishing a set of user profile rules relating to said conferences;
   c) collecting skills and profile information according to said business rules and said user profile rules from users who will potentially be matched for a conference;
   d) alerting matched conference participants to the time and date of the perspective conference;
   e) conducting the conference according to said business rules;
   f) recording the conference for future verification of compliance and agreement; and
   g) providing a feedback mechanism for the conference participants.

22. The method recited in claim 21 wherein said business rules comprise a step for allowing conference users to define conditions for their participation.

23. The method recited in claim 21 wherein said business rules comprise a step for allowing conference content to be pre-defined.

24. The method recited in claim 21 wherein said feedback mechanism comprises a step for defining what information about the conference is obtained from the conference users after the conference is terminated and storing said information with said business rules and said user profile rules for future conferences.

25. The method recited in claim 21 further comprising the step of h) forming a queue comprising prospectively matched users based on said business rules and user profile rules.

26. The method recited in claim 25 that further includes step i) comprises the step of allowing members of said queue to either opt-in or opt-out of a prospective conference.

27. The method recited in claim 21 further comprising the step of tracking objective data related to a conference including identity of users, length of conference, when the conference occurred, how each party to the conference entered and exited the conference and adding said objective data to said business rules.

28. The method recited in claim 21 wherein said conference is for the purpose of providing interpreting services to at least one conference participant.

29. The method recited in claim 21 wherein said conference is for the purpose of providing signing services to at least one conference participant where verbal or written communication does not establish contractual agreement.

30. The method recited in claim 21 wherein said conference is for the purpose of providing professional consulting services to at least one conference participant.

31. The method recited in claim 30 wherein said professional consulting services are medical care services, legal representation services, interpolator, or specialist services.

* * * * *